United States Patent [19]
Breton et al.

[11] Patent Number: 6,060,061
[45] Date of Patent: May 9, 2000

[54] METHOD FOR PREVENTING OR TREATING DISORDERS INVOLVING AN INFLAMMATORY PROCESS

[75] Inventors: Lionel Breton, Versailles; Richard Martin, Rochecorbon; Nathalie Pineau, Poitiers, all of France

[73] Assignee: Societe L'Oreal S.A., Paris, France

[21] Appl. No.: 08/981,591

[22] PCT Filed: Jul. 11, 1997

[86] PCT No.: PCT/FR97/01288

§ 371 Date: Mar. 9, 1998

§ 102(e) Date: Mar. 9, 1998

[87] PCT Pub. No.: WO98/04276

PCT Pub. Date: Feb. 5, 1998

[30] Foreign Application Priority Data

Jul. 30, 1996 [FR] France .................................. 96 09593

[51] Int. Cl.⁷ .................................................. A01N 65/00
[52] U.S. Cl. ........................................................ 424/195.1
[58] Field of Search ........................................... 424/195.1

[56] References Cited

FOREIGN PATENT DOCUMENTS

WO 93//25209  12/1993  WIPO .

OTHER PUBLICATIONS

Jain et al "In Vitro Production of essential oil from Proliferating Shoots of *Rosmarinus officinalis*" Planta Med 57 (1991) pp. 122–124.

Computer Abstract Japan 01102027 Michiko "Production of Antiallergic Drug", Jan. 19, 1989.

Offord et al "Rosemary components inhibit benzo[a]pyrene–induced genotoxicity in human bronchial cells" Carcinogenesis vol. 16, No. 9. pp. 2057–2062 (1995).

*Primary Examiner*—Herbert J. Lilling
*Attorney, Agent, or Firm*—Burns, Doane, Swecker & Mathis, L.L.P.

[57] ABSTRACT

The subject of the present invention is an extract of at least one plant of the Labiatae family, the said plant being cultured in vitro.

Its subject is also a cosmetic or pharmaceutical composition comprising, as active ingredient, at least an effective quantity of the said extract. The invention finally relates to the use of such an extract in a cosmetic composition or for the preparation of a pharmaceutical composition for controlling disorders involving an inflammatory process or an allergic process, and a process of cosmetic treatment involving such an extract.

41 Claims, No Drawings

METHOD FOR PREVENTING OR TREATING DISORDERS INVOLVING AN INFLAMMATORY PROCESS

The subject of the present invention is, in the most general aspect, an extract of at least one plant of the Labiatae family, the said plant being cultured in vitro.

It also relates to a cosmetic or pharmaceutical composition comprising, as active ingredient, at least an effective quantity of such an extract, the use, in a cosmetic composition or for the preparation of a pharmaceutical composition, as active ingredient for controlling disorders involving an inflammatory process or an allergic process, of an effective quantity of at least such an extract and a process of cosmetic treatment involving such an extract.

Later in the text, the expression "Labiatae extract" will have the same meaning as "extract of at least one plant of the Labiatae family".

Inflammation (or an inflammatory process) is a combination of biological reactions which is present in the entire animal kingdom. In man, two diseases out of three exhibit an inflammatory syndrome. The inflammation may be localized. It can be defined as the first response to any local aggression by a series of nonspecific reactions which are triggered regardless of the initial cause and which occur in three phases: vascular, cellulovascular and tissue fibrosis.

Swelling, pain, reddening, and heat are the terms which can be used to describe localized inflammation. These are generally due to infiltration of the injured tissues by an edema and/or vasodilation, that is dilation of the capillaries.

The signs of inflammation may extend to fever, a state of general discomfort and/or an increase in the concentration of certain blood plasma proteins.

It is a phenomena which involves, inter alia, a series of local cellular reactions and the release of cytokines and other mediators such as substance P, the prostaglandins, leukotrienes, bradykinin, histamine or serotonin.

It is also manifested by a modification of blood flow with, at the level of the damaged site, an increase in vascular permeability causing leakage of plasma proteins and of cells into the extracellular fluid, as well as extravasation of leucocytes, mainly neutrophil leucocytes and macrophages towards the inflammatory site.

These phenomena are in fact the result of the action of inflammation mediators.

Among the factors involved in these inflammatory phenomena, there may be mentioned cytokines including in particular interleukin-1α, interleukin-1β, interleukin-6, tumor necrosis factors α and β (TNF-α and -β), chemokines such as interleukin-8 or monocyte chemotactic and activating factor (MCAF), or other chemotactic factors responsible for the recruitment of lymphocytic, monocytic, Langerhans' or basophilic cells at the level of the inflammatory site such as B-4 leukotrienes or other factors involved in the inflammatory cascade, such as arachidonate acid, prostaglandins, including in particular the E2 prostaglandins.

Inflammatory phenomena are associated with numerous pathologies. There may be mentioned, by way of example, rheumatic conditions such as acute articular rheumatism, rheumatoid arthritis, pulmonary conditions such as emphysema, articular conditions such as arthrosis, tendinitis, periarthritis, spondylarthropathies or articular impairments of chronic enteropathies, allergies, inflammatory phases of alopecia, skin conditions such as sensitive skin, erythemas, in particular due to ultraviolet radiation, pruritus, erythema nodosum, urticaria, systemic mastocytosis, psoriasis, insect bites, other dermatological conditions such as atrophic polychondritis, erythemalgia, necrobiosis lipoidica or disseminated lupus erythematosus.

In the allergic processes, the early factors involved are also cytokines, particularly interleukin-1α and interleukin-1β and type α tumor necrosis factor (TNFα).

Unlike an inflammatory reaction, an allergic reaction is a phenomenon which responds to an external factor or an allergen. It is, in this case, a specifically immunological process which occurs only when an allergen is present and which affects only sensitized subjects.

However, the final result of an allergic reaction also leads to an acute inflammatory reaction, generally combined with an edema.

Whatever the phenomenon envisaged, there is a common point between all these mechanisms which leads to an inflammatory reaction of which the terminal facet can be measured by the release, by the mast cells of the skin, of at least one inflammation mediator such as histamine, serotonin, heparin, leukotrienes, prostaglandins, cytokines, nitrogen monoxide or reactive oxygenated species.

Substances which make it possible to treat inflammation or allergy have been sought for many years in the pharmaceutical industry. In this regard, there are many which have already been described, known in the literature by the names steroid or non-steroid anti-inflammatory drugs (SAID or NSAID) and a description of which can be found in, for example, the book by Schorderet and Dayer "Pharmacologie, Des concepts fondamentaux aux applications thérapeutiques", 1992, chapter 37, pages 541–561, 2nd edition, Frison-Roche/Slatkine publishers.

In addition to the fact that the known anti-inflammatory agents often exhibit substantial side effects, it remains important to have new products with anti-inflammatory activity.

The aim of the present invention is therefore to be able to provide a new product exhibiting an anti-inflammatory or anti-allergic activity and capable of not exhibiting notable side effects.

This aim and others are achieved by the present invention whose subject is an extract of at least one plant of the Labiatae family, characterized in that the said plant is cultured in vitro.

The anti-inflammatory effect of an extract of plants of the Labiatae family is known per se. There may be mentioned, in this regard, patent applications FR-A-2504551, JP-A-7017846, WO-A-9325209, SU-A-1733000, FR-A-2662078, DE-A-3536342, U.S. Pat. No. 5,393,526.

However, surprisingly and unexpectedly, the applicant has discovered that an extract of a plant of the Labiatae family, the said plant being cultured in vitro, exhibits an anti-inflammatory activity superior to that exhibited by an extract of a whole plant cultured in vivo. There will be found, moreover, in the text the results of experiments of binding to the receptors of inflammation mediators which establish these facts.

Accordingly, the subject of the invention is an extract of at least one plant of the Labiatae family, characterized in that the plant is cultured in vitro.

The selection pressure imposed by the physicochemical conditions during the growth of the plant cells in vitro makes it possible to obtain a standardized plant material available throughout the year contrary to plants cultured in vivo.

In vitro culture also is understood to mean the range of techniques known to a person skilled in the art which makes it possible artificially to obtain a plant or a part of a plant.

The plant material used in the invention may be any plant material obtained by in vitro culture. This is thus understood to mean the whole plant or a specific organ. In particular, the plant material may be plant cells and, still more particularly, undifferentiated (or dedifferentiated) plant cells.

Undifferentiated plant cells are understood to mean any plant cell exhibiting none of the traits of a specific specialization and capable of living by itself and not in dependence with other cells. These undifferentiated plant cells are possibly capable, under the effect of induction, of any differentiation consistent with their genome.

Depending on the chosen method of culture, and in particular depending on the chosen culture medium, it is possible to obtain, from the same explant, undifferentiated plant cells exhibiting different characters.

The Labiatae family comprises about 2700 species.

Thus, the extract of the invention may be prepared from a plant material of a labiate chosen from the genera Lavandula, Mentha, Preslia, Lycopus, Origanum, Thymus, Hyssopus, Satureia, Micromeria, Calamentha, Melissa, Horminium, Rosmarinus, Salvia, Nepeta, Dracocephalum, Glechoma, Lamium, Leonurus, Galeopsis, Stachys, Betonica, Ballota, Phlomis, Sideritis, Marrubium, Melittis, Scutellaria, Brunella, Ajuga and Teucrium.

Preferably, the extract of the invention may be prepared from plant material of a labiate chosen from the genera Lavandula, Mentha, Preslia, Origanum, Thymus, Melissa, Rosmarinus and Salvia, and still more preferably obtained from the genus Rosmarinus.

The extract of the invention may be prepared from plant material obtained from a species chosen from *Lavandula spica, Origanum vulgare, Thymus vulgaris, Melissa officinalis* or *Rosmarinus officinalis*.

More particularly, according to the invention, the extract is prepared from plant material obtained from *Rosmarinus officinalis*.

According to the invention, the extract of at least one labiate may be any extract prepared from plant material derived from the Labiatae family, cultured in vitro.

Any extraction method known to persons skilled in the art may be used to prepare the extract according to the invention.

There may be mentioned, in particular, alcoholic, in particular ethanolic or aqua-alcoholic, extracts.

It is also possible to use an extract prepared by the method described in French patent application No. 95-02379 filed by the applicant.

Thus, in a first step, the plant material is ground in an aqueous solution at low temperature, in a second step, the particles in suspension are removed from the aqueous solution derived from the first step, and in a third step, the aqueous solution derived from the second step is sterilized. This aqueous solution corresponds to the extract.

This extract may then be freeze-dried.

The first step may be advantageously replaced by a simple operation of freezing the plant tissues (for example at −20° C.), followed by an aqueous extraction based on the second and third steps described above.

If the plant material is whole plant, the fresh material to be treated is converted to the dry weight so as to be under the same extraction conditions as in vitro. The various parts of the plant are removed according to the relative weight of each part thereof.

The treatment at low temperature makes it possible to freeze the enzymatic activities, sterilizing filtration avoids degradation of the active agents by environmental microorganisms. Finally, the water vehicle is compatible with the receptors ex vivo and facilitates the cosmetic or pharmaceutical formulations.

It is known that plant extracts contain oxidases responsible, inter alia, for the oxidation of the said extracts. Now, such an oxidation leads to a dark brown color of the extracts and to a pungent odor, making them poorly compatible with their use in cosmetics. In this line of thought, a laccase is known in particular whose molecular weight is greater than 100,000 daltons.

Thus, advantageously, the extract obtained may be fractionated by any known method of fractionation which makes it possible to remove oxidases, and in particular polyphenoloxidase. The extract of the invention may, for example, be filtered on a dialysis membrane in order to remove therefrom the molecules with a molecular weight greater than 100,000 daltons. It is also possible to subject the extract to fractionation by selective precipitations.

Other methods make it possible to guard against oxidation phenomena. In particular, the extract can also be stabilized. Any known method of stabilization can be used according to the invention. It is possible, for example, to stabilize the extract of the invention by adding thereto cysteine in a final concentration of between 0.5 g/l and 10 g/l and preferably between 1.5 g/l and 2.5 g/l.

Obviously, the extract according to the invention can be fractionated and stabilized.

An example of preparing an extract which can be used according to the invention is given, moreover, in the examples.

The subject of the invention is also a cosmetic or pharmaceutical composition comprising, in a cosmetically or pharmaceutically acceptable medium, as active ingredient, at least one extract of at least one labiate, as defined above.

The pharmaceutical composition is preferably a dermatological composition.

The quantity of extract contained in the composition of the invention of course depends on the desired effect and may therefore vary to a large extent.

To give an order of magnitude, if the composition is a cosmetic composition, it may contain an extract as defined above in a quantity representing from 0.001% to 50% of the total weight of the composition and preferably in a quantity representing from 0.005% to 25% of the total weight of the composition.

To give an order of magnitude, if the composition is a pharmaceutical composition, it may contain an extract as defined above in a quantity representing from 0.01% to 70% of the total weight of the composition and preferably in a quantity representing from 0.05% to 40% of the total weight of the composition.

Examples of disorders involving an inflammatory process were seen earlier in the text.

These inflammatory disorders may be cutaneous or systemic.

Thus, the compositions according to the invention are intended to control cutaneous or systemic disorders involving an inflammatory process.

In particular, the compositions according to the invention are intended to control rheumatic conditions such as acute articular rheumatism, rheumatoid arthritis, pulmonary conditions such as emphysema, articular conditions such as arthrosis, tendinitis, periarthritis, spondylarthropathies or articular impairments of chronic enteropathies, allergies, inflammatory phases of alopecia, skin conditions such as sensitive skin, erythemas, in particular due to ultraviolet radiation, pruritus, erythema nodosum, urticaria, systemic mastocytosis, psoriasis, insect bites, or other dermatological conditions such as atrophic polychondritis, erythemalgia, necrobiosis lipoidica. There may also be mentioned disseminated lupus erythematosus.

Still more preferably, the compositions according to the invention are intended to control skin irritations and/or dartres and/or dysesthetic sensations and/or sensations of overheating and/or pruritus of the skin and/or of the mucous membranes.

The composition according to the invention can be ingested, injected or applied to the skin (over any cutaneous region of the body), the hair, the nails or the mucous membranes such as (buccal, jugal, gingival, genital, or conjunctival). Depending on the mode of administration, the composition according to the invention may be provided in any of the galenical forms normally used.

For a topical application to the skin, the composition may take the form, in particular, of an aqueous or oily solution or of a dispersion of the lotion or serum type, of emulsions of liquid or semi-liquid consistency of the milk type, obtained by dispersion of a fatty phase in an aqueous phase (O/W) or conversely (W/O), or of suspensions or emulsions of soft consistency of the aqueous or anhydrous cream or gel type, or of microcapsules or microparticles, or of vesicular dispersions of the ionic and/or nonionic type. These compositions are prepared according to the customary methods.

They can also be used for the hair, in the form of aqueous, alcoholic or aqueous/alcoholic solutions, or in the form of creams, gels, emulsions, mousses or in the form of aerosol compositions also comprising a pressurized propellant.

For injection, the composition may be provided in the form of an aqueous or oily lotion or in the form of a serum. For the eyes, it may be provided in the form of drops, and for ingestion, it may be provided in the form of capsules, granules, syrups or tablets.

The quantities of the various constituents of the compositions according to the invention are those conventionally used in the fields considered.

These compositions constitute in particular cleansing, protective, treatment or care creams for the face, for the hands, for the feet, for the large anatomical folds or for the body, (for example day creams, night creams, makeup removing creams, foundation creams, antisun creams), fluid foundations, makeup removing milks, protective or care body milks, antisun milks, skin care lotions, gels or foams, such as lotions for cleansing, antisun lotions, artificial tanning lotions, bath compositions, deodorant compositions containing a bactericidal agent, aftershave gels or lotions, depilatory creams, compositions against insect bites, antipain compositions or compositions for treating certain skin diseases such as eczema, rosacea, psoriasis, lichens and severe pruritus.

The composition according to the invention may also consist of solid preparations constituting cleansing soaps or cakes.

The composition may also be packaged in the form of an aerosol composition also containing a pressurized propelling agent.

The composition according to the invention may also be a composition for hair care, especially a shampoo, hair setting lotion, a treatment lotion, a hair styling cream or gel, a dyeing (especially oxidation dyeing) composition optionally in the form of dyeing shampoos, restructuring lotions for the hair, a permanent waving composition (especially a composition for the first stage of a permanent waving), a lotion or gel against hair loss, an antiparasitic shampoo, and the like.

The composition may also be for dentibuccal use, for example a toothpaste. In this case, the composition may contain customary adjuvants and additives for compositions for buccal use and especially surfactants, thickening agents, humectants, polishing agents such as silica, various active ingredients such as fluorides, in particular sodium fluoride, and optionally sweetening agents such as sodium saccharinate.

When the composition is an emulsion, the proportion of fatty phase may range from 5% to 80% by weight, and preferably from 5% to 50% by weight relative to the total weight of the composition. The oils, waxes, emulsifiers and coemulsifiers used in the composition in the form of an emulsion are chosen from those conventionally used in the cosmetic field. The emulsifier and the coemulsifier are present in the composition in a proportion ranging from 0.3% to 30% by weight, and preferably from 0.5 to 20% by weight relative to the total weight of the composition. The emulsion may, in addition, contain lipid vesicles.

When the composition is an oily gel or a solution, the fatty phase may represent more than 90% of the total weight of the composition.

In a known manner, the cosmetic composition may also contain adjuvants common in the cosmetic field, such as hydrophilic or lipophilic gelling agents, hydrophilic or lipophilic additives, preservatives, antioxidants, solvents, perfumes, fillers, screening agents, odor absorbers and coloring matter. The quantities of these various adjuvants are those conventionally used in the cosmetic field, and for example from 0.01% to 10% of the total weight of the composition. These adjuvants, depending on their nature, may be introduced into the fatty phase, into the aqueous phase and/or into the lipid spherules.

As oils or waxes which can be used in the invention, there may be mentioned mineral oils (petroleum jelly), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswaxes, carnauba or paraffin waxes. Fatty alcohols and fatty acids (stearic acid) may be added to these oils.

As emulsifiers which can be used in the invention, there may be mentioned for example glycerol stearate, polysorbate 60 and the PEG-6/PEG-32/Glycol Stearate mixture sold under the name Tefose® 63 by the company Gattefosse.

As solvents which can be used in the invention, there may be mentioned the lower alcohols, especially ethanol and isopropanol, propyleneglycol.

As hydrophilic gelling agents which can be used in the invention, there may be mentioned the carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, there may be mentioned modified clays such as bentones, metal salts of fatty acids such as aluminium stearates and hydrophobic silica, ethylcellulose, polyethylene.

The composition may contain other hydrophilic active agents, such as proteins or protein hydrolysates, amino acids, polyols, urea, allantoin, sugars and sugar derivatives, water-soluble vitamins, plant extracts and hydroxy acids.

As lipophilic active agents, there may be used retinol (vitamin A) and its derivatives, tocopherol (vitamin E) and its derivatives, essential fatty acids, ceramides, essential oils, salicylic acid and its derivatives.

According to the invention, the composition may combine at least one extract of at least one labiate with other active agents intended especially for the prevention and/or treatment of skin conditions. Among these active agents, there may be mentioned, by way of example:

agents modulating skin differentiation and/or proliferation and/or pigmentation such as retinoic acid and its isomers, retinol and its esters, vitamin D and its derivatives, estrogens such as estradiol, kojic acid or hydroquinone;

antibacterials such as clindamycin phosphate, erythromycin or antibiotics of the tetracycline class;

antiparasitic agents, in particular metronidazole, crotamiton or pyrethrinoids;

antifungal agents, in particular the compounds belonging to the imidazole class such as econazole, ketoconazole or miconazole or their salts, the polyene compounds, such as amphotericin B, the compounds of the allylamine family, such as terbinafine, or octopirox;

antiviral agents such as acyclovir;

steroidal anti-inflammatory agents such as hydrocortisone, betamethasone valerate or clobetasol propionate, or nonsteroidal anti-inflammatory agents such as ibuprofen and its salts, diclofenac and its salts, acetylsalicylic acid, acetaminophen or glycyrrhetinic acid;

anesthetic agents such as lidocaine hydrochloride and its derivatives;

antipruritic agents such as thenaldine, trimeprazine or cyproheptadine;

keratolytic agents such as alpha- and beta-hydroxycarboxylic or beta-ketocarboxylic acids, their salts, amides or esters and more particularly hydroxy acids such as glycolic acid, lactic acid, salicylic acid, citric acid and, in general, fruit acids and 5-n-octanoylsalicylic acid;

anti-free radical agents, such as alpha-tocopherol or its esters, superoxide dismutases, certain metal chelators or ascorbic acid and its esters;

antiseborrheic agents such as progesterone;

antidandruff agents such as octopirox or zinc pyrithione;

anti-acne agents such as retinoic acid or benzoyl peroxide;

extracts of other plants and/or microorganisms.

Thus, according to a specific embodiment, the invention relates to a composition containing at least one extract of at least one labiate and at least one agent chosen from antibacterial, antiparasitic, antifungal, antiviral, anti-inflammatory, anti pruritic, anaesthetic, keratolytic, anti-free radical, antiseborrheic, antidandruff and anti-acne agents, and agents modulating skin differentiation and/or proliferation and/or pigmentation, extracts of other plants and/or microorganisms.

The subject of the invention is also the use, as active ingredient, in a cosmetic composition or for the preparation of a pharmaceutical composition, of an effective quantity of at least one extract as defined above for controlling disorders involving an inflammatory process as described above.

Advantageously, according to the invention, at least one extract of at least one labiate may be combined with products with an irritant effect which are used commonly in the cosmetic or pharmaceutical field, which products are sometimes cosmetically or pharmaceutically active agents. The presence of an extract of at least one labiate in a cosmetic or pharmaceutical composition comprising a product having an irritant effect makes it possible to strongly attenuate, or even suppress, this irritant effect.

This makes it possible, in addition, to increase the quantity of active ingredient with an irritant effect relative to the quantity of active ingredient normally used for an increased efficacy.

The invention relates more particularly to a cosmetic or pharmaceutical composition, characterized in that it comprises, in a cosmetically or pharmaceutically acceptable medium, at least one product with an irritant effect and at least one extract of at least one labiate.

As products with an irritant effect, there may be mentioned, for example and with no limitation being implied, surfactants (ionic or nonionic), preservatives, organic solvents or active agents such as α-hydroxy acids (citric, malic, glycolic, tartaric, mandelic or lactic acid), β-hydroxy acids (salicylic acid and its derivatives), α-keto acids, β-keto acids, retinoids (retinol, retinal, retinoic acid), anthralins (dioxyanthranol), anthranoids, peroxides (particularly benzoyl peroxide), minoxidil, lithium salts, antimetabolites, vitamin D and its derivatives, hair dyes or colorants (para-phenylenediamine and its derivatives, aminophenols), perfuming alcoholic solutions (perfume, toilet water, aftershave, deodorants), anti-perspirants (some aluminium salts), depilatory active agents or permanent-waving active agents (thiols), depigmenting active agents (hydroquinone).

Preferably, the invention relates to a cosmetic or pharmaceutical composition, characterized in that it comprises, in a cosmetically or pharmaceutically acceptable medium, at least one extract of at least one labiate and at least one product with an irritant effect chosen from active agents such as α-hydroxy acids (citric, malic, glycolic, tartaric, mandelic or lactic acid), β-hydroxy acids (salicylic acid and its derivatives), α-keto acids, β-keto acids, retinoids (retinol, retinal, retinoic acid), anthralins (dioxyanthranol), anthranoids, peroxides (particularly benzoyl peroxide), minoxidil, lithium salts, antimetabolites, vitamin D and its derivatives, hair dyes or colorants (para-phenylenediamine and its derivatives, aminophenols), anti-perspirants (some aluminium salts), depilatory active agents or permanent-waving active agents (thiols), depigmenting active agents (hydroquinone).

The use of at least one extract of at least one labiate makes it possible in particular to multiply 2- to 10-fold the quantity of active ingredient with an irritant effect compared with the state of the art, without feeling all the discomfort mentioned above. Thus, it is possible to use hydroxy acids up to 50% of the weight of the composition or retinoids up to 5%, by markedly reducing their irritant character.

The subject of the present invention is, in addition, a process of cosmetic treatment for reducing the irritant effect of a cosmetic composition, characterized in that a composition as described above is applied to the skin, to the hair and/or to the mucous membranes.

The process of cosmetic treatment of the invention can be carried out in particular by applying the hygiene or cosmetic compositions as defined above, according to the usual technique for using these compositions. For example: application of creams, gels, sera, lotions, make-up removing milks or antisun compositions to the skin or to dry hair, application of a hair lotion to wet hair, of shampoo or application of toothpaste to the gums.

The following examples and compositions illustrate the invention without limiting it in any way. In the compositions, the proportions indicated are percentages by weight.

EXAMPLE 1

Preparation of an Extract of Undifferentiated *Rosmarinus officinalis* Cells Cultured in vitro:

Under nitrogen, undifferentiated *Rosmarinus officinalis* cells cultured in vitro under axenic conditions are recovered by filtration on a 50 μm sieve after culturing in an Erlenmeyer flask or in a fermenter. 1 ml of demineralized water containing 1.8 g/l of cysteine is added to 1 g of fresh material thus obtained. The whole is ground (Potter, Ultra Turrax and the like) in a Turrax at 24,000 rpm for 1 minute at 4° C. (ice bath). The ground product is centrifuged for 15 minutes at 10,000 G at 4° C. The supernatant is filtered on 0.22 μm (sterilizing filtration).

The extract thus prepared is stored at 4° C. It contains about 15 g of dry material per liter.

The extract is then fractionated by ultrafiltration on a Sartorius-type membrane in order to free it of the oxidation phenomena.

An aqueous extract which can be used directly (aqueous extract) is thus obtained.

The extract is then freeze-dried (freeze-dried extract).

EXAMPLE 2

Pharmacological Activities of the Extracts of Example 1:

The receptor affinity of the *Rosmarinus officinalis* extracts was tested for the B2, IL-1β, IL-6, TNF and H1 receptors:

The measurement of the receptor affinity of the *Rosmarinus officinalis* extract for the B2 receptor was carried out according to the method described in the article: Burch, R. M. et al. Biotech update (DuPont NEN), 7: 3–11; (1992).

The measurement of the receptor affinity of the *Rosmarinus officinalis* extract for the IL-1β receptor was carried out according to the method described in the article: Bird, T. A. et al., FEBS Letter, 225: 21–26; (1987).

The measurement of the receptor affinity of the *Rosmarinus officinalis* extract for the IL-6 receptor was carried out according to the method described in the article: Taga, T. et al., J. Exp. Med., 166: 967–981; (1987)

The measurement of the receptor affinity of the *Rosmarinus officinalis* extract for the TNF receptor was carried out according to the method described in the article: Brockhaus, M. et al., P.N.A.S., 87: 3127–3131; (1990).

The measurement of the receptor affinity of the *Rosmarinus officinalis* extract for the H1 receptor was carried out according to the method described in the article: Dini S. et al., Agents and Actions, 33: 181–184; (1991).

The extracts prepared according to Example 1 were tested at the concentrations of 0.5%, 2% and 5%.

During each experiment, the reference molecule for the receptor studied (NPC 567 for the B2 receptor, IL-1β for the IL-1β receptor, IL-6 for the IL-6 receptor, TNFα for the TNF receptor and pyrilamine for the H1 receptor) is tested in parallel at 8 concentrations (n=2) in order to obtain a standard curve which makes it possible to validate the experiment.

The results of these experiments are summarized in the table below: these results are expressed in percentage inhibition of binding calculated relative to the control.

| | | | | extract of | | | | | | | |
|---|---|---|---|---|---|---|---|---|---|---|---|
| | | | | | undifferentiated cells nonstabilized | | | undifferentiated cells stabilized extract | | | undifferentiated cells extract filtered at 100,000 | |
| lig- | whole plant | | | | | | | | | | |
| and | 0.5% | 2% | 5% | 0.5% | 2% | 5% | 0.5% | 2% | 5% | 2% | 5% |
| B2 | 15 | 46 | 68 | 16 | 46 | 59 | 43 | 62 | 82 | nd | nd |
| IL-1β | — | — | 10 | 17 | 66 | 79 | 11 | 77 | 97 | 50 | 78 |
| IL-6 | — | — | — | 48 | 80 | 100 | 31 | 88 | 100 | 88 | 119 |
| TNF | — | — | — | 11 | 64 | 82 | 16 | 63 | 87 | 49 | 65 |
| H1 | 48 | 89 | 95 | 13 | 49 | 82 | 41 | 79 | 95 | nd | nd |

—: <10%.
Nd: not determined.

The results of these experiments demonstrate an affinity of the *Rosmarinus officinalis* extract for the receptors of the inflammation mediators. More particularly, the extracts of undifferentiated cells exhibit good affinity for several receptors for inflammation mediators.

The extracts stabilized and/or filtered in order to inhibit and/or remove certain enzymes, in particular the oxidases, retained their affinity for the receptors for the inflammation mediators.

These extracts are good pluripotent anti-inflammatory agents.

EXAMPLE 3

Examples of formulations illustrating the invention and particularly the compositions according to the invention combining at least one extract of *Rosmarinus officinalis* and a product with an irritant effect. These compositions were obtained simply by mixing the various components.

Composition 1: make-up removing lotion for the face

| | |
|---|---|
| Extract of Example 1 (aqueous form) | 10.00% |
| Antioxidant | 0.05% |
| Isopropanol | 40.00% |
| Preservative | 0.30% |
| Water        qs | 100.00% |

Composition 2: shampoo

| | |
|---|---|
| Extract of Example 1 (aqueous form) | 5.00% |
| Hydroxypropylcellulose (Klucel H sold by the company Hercules) | 1.00% |
| Perfume | 0.50% |
| Preservative | 0.30% |
| Water        qs | 100.00% |

Composition 3: face care cream (oil-in-water emulsion)

| | |
|---|---|
| Extract of Example 1 (freeze-dried form) | 0.20% |
| Glycerol stearate | 2.00% |
| Polysorbate 60 (Tween 60 sold by the company ICI) | 1.00% |

-continued

| | | |
|---|---|---|
| Stearic Acid | | 1.40% |
| Triethanolamine | | 0.70% |
| Carbomer | | 0.40% |
| Liquid fraction of shea butter | | 12.00% |
| Perhydrosqualene | | 12.00% |
| Antioxidant | | 0.05% |
| Perfume | | 0.50% |
| Preservative | | 0.30% |
| Water | qs | 100.00% |

Composition 4: gel for the treatment of acne

| | | |
|---|---|---|
| Extract of Example 1 (freeze-dried form) | | 0.50% |
| All-trans-retinoic acid | | 0.05% |
| Hydroxypropylcellulose (Klucel H sold by the company Hercules) | | 1.00% |
| Antioxidant | | 0.05% |
| Isopropanol | | 40.00% |
| Preservative | | 0.30% |
| Water | qs | 100.00% |

Composition 5: face care gel

| | | |
|---|---|---|
| Extract of Example 1 (aqueous form) | | 5.00% |
| Hydroxypropylcellulose (Klucel H sold by the company Hercules) | | 1.00% |
| Antioxidant | | 0.05% |
| Isopropanol | | 40.00% |
| Preservative | | 0.30% |
| Water | qs | 100.00% |

Composition 6: anti-pain gel

| | | |
|---|---|---|
| Extract of Example 1 (aqueous form) | | 10.00% |
| Hydroxypropylcellulose (Klucel H sold by the company Hercules) | | 1.00% |
| Antioxidant | | 0.05% |
| Lidocaine hydrochloride | | 2.00% |
| Isopropanol | | 40.00% |
| Preservative | | 0.30% |
| Water | qs | 100.00% |

Composition 7: solar erythema care cream (oil-in-water emulsion)

| | | |
|---|---|---|
| Extract of Example 1 (freeze-dried form) | | 0.50% |
| Glycerol stearate | | 2.00% |
| Polysorbate 60 (Tween 60 sold by the company ICI) | | 1.00% |
| Stearic acid | | 1.40% |
| Glycyrrhetinic acid | | 2.00% |
| Triethanolamine | | 0.70% |
| Carbomer | | 0.40% |
| Liquid fraction of shea butter | | 12.00% |
| Sunflower oil | | 10.00% |
| Antioxidant | | 0.05% |
| Perfume | | 0.50% |
| Preservative | | 0.30% |
| Water | qs | 100.00% |

Composition 8: anti-wrinkle care cream for the face (oil/water emulsion)

| | | |
|---|---|---|
| Extract of Example 1 (aqueous form) | | 5.00% |
| Glycerol stearate | | 2.00% |
| Polysorbate 60 (Tween 60 sold by the company ICI) | | 1.00% |
| Stearic acid | | 1.40% |
| 5-n-Octanoylsalicylic acid | | 0.50% |
| Triethanolamine | | 0.70% |
| Carbomer | | 0.40% |
| Liquid fraction of shea butter | | 12.00% |
| Perhydrosqualene | | 12.00% |
| Antioxidant | | 0.05% |
| Perfume | | 0.50% |
| Preservative | | 0.30% |
| Water | qs | 100.00% |

Composition 9: lotion for removing scars due to acne

| | | |
|---|---|---|
| Extract of Example 1 (aqueous form) | | 5.00% |
| Glycolic acid | | 50.00% |
| Hydroxypropylcellulose (Klucel H sold by the company Hercules) | | 0.05% |
| Preservative | | 0.30% |
| NaOH | | qs pH = 2.8 |
| Ethanol | | qs 100.00% |

We claim:

1. A method for preventing or treating disorders involving an inflammatory process, said process comprising administering an effective amount of at least one extract of at least one plant of the Labiatae family to prevent or treat disorders involving an inflammatory process to a patient in need thereof, wherein said plant is cultured in vitro, and wherein said plant extract is obtained by a process comprising culturing cells derived from Rosmarinus cells in vitro; grinding said cells; centrifuging the resultant ground product at about 4° C.; and sterilizing the resultant supernatant by filtration.

2. The method of claim 1, wherein said plant is a labiate of the genus comprising Lavandula, Mentha, Preslia, Lycopus, Origanum, Thymus, Hyssopus, Satureia, Micromeria, Calamentha, Melissa, Horminium, Rosmarinus, Salvia, Nepeta, Dracocephalum, Glechoma, Lamium, Leonurus, Galeopsis, Stachys, Betonica, Ballota, Phlomis, Sideritis, Marrubium, Melittis, Scutellaria, Brunella, Ajuga or Teucrium.

3. The method of claim 1, wherein said plant is a labiate of the genus comprising Lavandula, Mentha, Preslia, Origanum, Thymus, Melissa, Rosmarinus or Salvia.

4. The method of claim 3, wherein said plant is a labiate of the genus Rosmarinus.

5. The method of claim 4, wherein said plant is *Rosmarinus officinalis*.

6. The method of claim 1, wherein the plant cells are undifferentiated cells.

7. The method of claim 1, wherein the extract is fractionated and oxidases are removed.

8. The method of claim 1, wherein said extract is in the form of a composition comprising an extract and a cosmetically and/or pharmaceutically acceptable carrier therefor.

9. The method of claim 8, wherein said extract is present in an amount ranging from 0.001% to 50% of the total weight of a cosmetic composition.

10. The method of claim 8, wherein said extract is present in an amount ranging from 0.01% to 70% of the total weight of a pharmaceutical composition.

11. The method of claim 1, wherein said disorder involving an inflammatory process is selected from the group consisting of rheumatic conditions, pulmonary conditions, articular conditions, allergies, the inflammatory phases of alopecia, skin conditions and insect bites.

12. The method of claim 1, wherein said disorder involving an inflammatory process is selected from the group consisting of skin irritations, dartres, or dysesthetic sensations, sensations of overheating and pruritus of the skin or of the mucous membranes.

13. The method of claim 1, wherein the extract is freeze dried.

14. The method of claim 1, wherein the extract is filtered using a dialysis membrane in order to remove molecules having a molecular weight greater than 100,000 daltons.

15. A plant extract for preventing or treating disorders involving an inflammatory process obtained by obtaining an in vitro culture comprising undifferentiated cells derived from at least one plant of the Labiatae family; grinding said cells; centrifuging the resultant ground product; sterilizing the resultant supernatant by filtration; and fractionating the extract to remove oxidases.

16. The plant extract of claim 15, wherein said plant is a labiate of the genus comprising Lavandula, Mentha, Preslia, Lycopus, Origanum, Thymus, Hyssopus, Satureia, Micromeria, Calamentha, Melissa, Horminium, Rosmarinus, Salvia, Nepeta, Dracocephalum, Glechoma, Lamium, Leonurus, Galeopsis, Stachys, Betonica, Ballota, Phlomis, Sideritis, Marrubium, Melittis, Scutellaria, Brunella, Ajuga or Teucrium.

17. The plant extract of claim 16, wherein said plant is a labiate of the genus comprising Lavandula, Mentha, Preslia, Origanum, Thymus, Melissa, Rosmarinus or Salvia.

18. The plant extract of claim 17, wherein said plant is a labiate of the genus Rosmarinus.

19. The plant extract of claim 18, wherein said plant is *Rosmarinus officinalis*.

20. The plant extract of claim 15, wherein said extract is in the form of a composition comprising a said plant extract and a cosmetically and/or pharmaceutically acceptable carrier therefor.

21. The plant extract of claim 20, wherein said extract is present in an amount ranging from 0.001% to 50% of the total weight of a cosmetic composition.

22. The plant extract of claim 20, wherein said extract is present in an amount ranging from 0.01% to 70% of the total weight of a pharmaceutical position.

23. The plant extract of claim 15, wherein said disorder involving an inflammatory process is selected from the group consisting of rheumatic conditions, pulmonary conditions, articular conditions, allergies, the inflammatory phases of alopecia, skin conditions and insect bites.

24. The plant extract of claim 15, wherein said disorder involving an inflammatory process is selected from the group consisting of skin irritations, dartres, or dysesthetic sensations, sensations of overheating and pruritus of the skin or of the mucous membranes.

25. The plant extract of claim 15, wherein the extract is freeze dried.

26. The plant extract of claim 15, wherein the plant extract is filtered using a dialysis membrane in order to remove molecules having a molecular weight greater than 100,000 daltons.

27. A cosmetic or pharmaceutical composition comprising at least one extract of claim 15, at least one compound having an irritant effect and a cosmetically or pharmaceutically acceptable carrier therefor.

28. The cosmetic or pharmaceutical composition of claim 27, wherein said compound having an irritant effect comprises an ionic surfactant, non-ionic surfactant, a preservative, an organic solvent, an alpha-hydroxy acid or derivative thereof, a beta-hydroxy acid or derivative thereof, an alpha-keto acid, a beta-keto acid, a retinoid, an anthralin, an anthanoid, a peroxide, minoxidil, a lithium salt, an antimetabolite, vitamin D or its derivative, a hair dye, a hair colorant, a perfuming alcoholic solution, an anti-perspirant, a depilatory, a permanent-waving agent, or a depigmenting agent.

29. The cosmetic or pharmaceutical composition of claim 27, wherein the composition is formulated for application to the skin, the hair and/or to the mucous membranes.

30. A plant extract for preventing or treating disorders involving an inflammatory process obtained by obtaining an in vitro culture comprising undifferentiated cells derived from at least one plant of the Labiatac family; grinding said cells; centrifuging the resultant ground product; sterilizing the resultant supernatant by filtration; and filtering said extract using a dialysis membrane in order to remove molecules having a molecular weight greater than 100,000 daltons.

31. The plant extract of claim 30, wherein said plant is a labiate of the genus comprising Lavandula, Mentha, Preslia, Lycopus, Origanum, Thymus, Hyssopus, Satureja, Micromeria, Calamentha, Melissa, Horminium, Rosmarinus, Salvia, Nepeta, Dracocephalum, Glechoma, Lamium, Leonurus, Galeopsis, Stachys, Betonica, Ballota, Phlomis, Sideritis, Marrubium, Melittis, Scutellaria, Brunella, Ajuga or Teucrium.

32. The plant extract of claim 31, wherein said plant is a labiate of the genus comprising Lavandula, Mentha, Preslia, Origanum, Thymus, Melissa, Rosmarinus or Salvia.

33. The plant extract of claim 32, wherein said plant is a labiate of the genus Rosmarinus.

34. The plant extract of claim 32, wherein said plant is *Rosmarinus officinalis*.

35. The plant extract of claim 30, wherein said extract is in the form of a composition comprising a said plant extract and a cosmetically and/or pharmaceutically acceptable carrier therefor.

36. The plant extract of claim 30, wherein said disorder involving an inflammatory process is selected from the group consisting of rheumatic conditions, pulmonary conditions, articular conditions, allergies, the inflammatory phases of alopecia, skin conditions and insect bites.

37. The plant extract of claim 30, wherein said disorder involving an inflammatory process is selected from the group consisting of skin irritations, dartres, or dysesthetic sensations, sensations of overheating and pruritus of the skin or of the mucous membranes.

38. The plant extract of claim 30, wherein the extract is freeze dried.

39. A cosmetic or pharmaceutical composition comprising at least one extract of claim 30, at least one compound having an irritant effect and a cosmetically or pharmaceutically acceptable carrier therefor.

40. The cosmetic or pharmaceutical composition of claim 39, wherein said compound having an irritant effect comprises an ionic surfactant, non-ionic surfactant, a preservative, an organic solvent, an alpha-hydroxy acid or derivative thereof, a beta-hydroxy acid or derivative thereof, an alpha-keto acid, a beta-keto acid, a retinoid, an anthralin, an anthanoid, a peroxide, minoxidil, a lithium salt, an antimetabolite, vitamin D or its derivative, a hair dye, a hair colorant, a perfuming alcoholic solution, an anti-perspirant, a depilatory, a permanent-waving agent, or a depigmenting agent.

41. The cosmetic or pharmaceutical composition of claim 39, wherein the composition is formulated for application to the skin, the hair and/or to the mucous membranes.

* * * * *